US009265588B2

(12) United States Patent
Schwan (10) Patent No.: US 9,265,588 B2
(45) Date of Patent: Feb. 23, 2016

(54) PATTERNED VISUALIZATION OF ELECTROPHYSIOLOGICAL DATA

(75) Inventor: Thomas Schwan, Geretsried (DE)

(73) Assignee: BRAINLAB AG, Kircheim, Heimstette (DE)

( * ) Notice: Subject to any disclaimer, the term of this patent is extended or adjusted under 35 U.S.C. 154(b) by 2389 days.

(21) Appl. No.: 11/107,296

(22) Filed: Apr. 15, 2005

(65) Prior Publication Data

US 2006/0235483 A1   Oct. 19, 2006

(51) Int. Cl.
| | |
|---|---|
| A61B 19/00 | (2006.01) |
| A61B 5/04 | (2006.01) |
| A61N 1/05 | (2006.01) |
| A61B 5/00 | (2006.01) |
| G06F 19/00 | (2011.01) |

(52) U.S. Cl.
CPC .............. *A61B 19/52* (2013.01); *A61B 5/6868* (2013.01); *A61B 5/04* (2013.01); *A61B 5/4082* (2013.01); *A61B 2019/5289* (2013.01); *A61N 1/0529* (2013.01); *A61N 1/0534* (2013.01); *G06F 19/3406* (2013.01)

(58) Field of Classification Search
CPC .............. A61N 1/0534; A61N 1/0529; A61N 1/37247; A61N 1/3615; A61N 1/36171; A61B 5/04001; A61B 5/6868; A61B 5/0478; A61B 2562/0209; A61B 5/0476; A61B 5/1101; A61B 19/50; A61B 19/5244; A61B 2019/507; A61B 5/4082; A61B 19/56; A61B 5/4064; A61B 5/0484; A61B 5/11; A61B 2019/502; A61B 2019/504; A61B 2576/026; A61B 5/04; G06F 19/3437; G06F 19/3406; G06F 19/3481; G06K 2209/057

USPC ............................. 600/407, 427; 607/45, 116
See application file for complete search history.

(56) References Cited

U.S. PATENT DOCUMENTS

| | | | | | |
|---|---|---|---|---|---|
| 5,687,737 | A | * | 11/1997 | Branham et al. | ............... 600/523 |
| 6,055,452 | A | * | 4/2000 | Pearlman | ...................... 600/547 |
| 6,421,560 | B1 | | 7/2002 | Yoo | |
| 6,868,171 | B2 | * | 3/2005 | Souluer | ......................... 382/128 |
| 7,343,205 | B1 | * | 3/2008 | Pianca et al. | ................... 607/116 |
| 7,355,597 | B2 | * | 4/2008 | Laidlaw et al. | ................ 345/419 |
| 2005/0043774 | A1 | * | 2/2005 | Devlin et al. | .................... 607/45 |
| 2005/0070781 | A1 | * | 3/2005 | Dawant et al. | ................ 600/407 |

FOREIGN PATENT DOCUMENTS

EP                1 396 233         9/2002

OTHER PUBLICATIONS

"Three-Dimensional Database of Subcortical Electrophysiology for Image-Guided Stereotactic Functional Neurosurgery"; IEEE Transactions on Medical Imaging, vol. 22, No. 1, Jan. 2003.

* cited by examiner

Primary Examiner — Katherine Fernandez
(74) Attorney, Agent, or Firm — Tucker Ellis, LLP; Michael Hudzinski (57) ABSTRACT

A system and method for graphically depicting a desired region for a treatment instrument with respect to a patient is disclosed. In performing the method, different types of electrophysiological data of the patient are obtained. The different types of electrophysiological data are combined to provide a graphical depiction that indicates the desired region for the treatment instrument.

30 Claims, 8 Drawing Sheets

FIG. 4B burstic activity detected by recording, discretely measured

PATTERNED VISUALIZATION OF ELECTROPHYSIOLOGICAL DATA

FIELD OF THE INVENTION

The present invention relates generally to analyzing electrophysiological data and, more specifically, to a system and method for graphically depicting a desired region for a treatment instrument with respect to a patient.

BACKGROUND OF THE INVENTION

Deep brain stimulation (DBS) is one method that can be used to treat Parkinson's disease. In DBS, a periodic stimulation signal is injected into the brain via an implanted electrode. Depending on the location of the stimulation probe and on the strength and shape of the stimulation signal, positive clinical results can be achieved.

To determine the location of the stimulation electrode, electrophysiological data is acquired during brain surgery using recording and stimulation devices. For example, a recording microelectrode and/or a stimulation electrode can be positioned within the brain. The recording microelectrode measures the electrical activity of neurons over a representative period of time and at a number of different positions within the brain, while the stimulation electrode is used to trigger activity of specific neurons in the brain and to measure the stimulated effect on the patient. This can be achieved by applying periodic electrical stimulation signals via the stimulation electrode to different positions within the brain. Depending on the strength, shape and location of the signal, the patient can have various responses, such as visual, speech, motor effects, and/or changes of Parkinson's symptoms, as well as conditional changes of the patient. The responses can be physically observed on and in cooperation with the patient and documented together with the responsible stimulation parameters.

The acquired data (stimulation and recording results) are analyzed by a neurologist and/or electrophysiologist, who localizes specific functional areas within the patient's brain. The neurologist and/or electrophysiologist determines the correlation between the recorded neuronal activity, specific stimulation effects, the position of the applied stimulation signal within the patient's brain, and the strength of the applied stimulation signal. Based on the data, an optimum location of the implanted electrode is identified. As used herein, an optimum location is a location that achieves the most sufficient clinical result for the patient. This includes a low severity of undesired stimulation side effects, e.g., numbness or parasthesia, while providing a high-degree of desired stimulation effects, e.g., tremor, rigor and akinesia improvement. Due to the large variation of observed electrophysiological aspects, a sufficient data assessment and visual evaluation of all data becomes very important.

Conventionally, electrophysiological data is intra-operatively recorded using paper protocols and processed post-operatively using standard tools, e.g., Microsoft Excel or Access, to obtain visual representations for each type of electrophysiological data. Each type of electrophysiological data may be represented graphically, such as a snapshot bitmap of a signal recording in relation to MR anatomy or a graph showing stimulation threshold in relation to stereotactic position. Processing the different types of data individually is useful for post-operative studies. However, such processing techniques are of little value for intra-operative decision making.

SUMMARY OF THE INVENTION

The present invention improves over the prior art by providing a system and method that easily, accurately and intra-operatively conveys a desired location for a treatment instrument with respect to a patient. The invention graphically depicts the desired location in a simple way, wherein a plurality of different types of electrophysiological data are combined in a summarized graphical depiction. A simple color coding scheme may be employed, wherein a first color, such as green, represents a desirable location, a second color, such as red, represents an undesirable location, and a third color, such as yellow, represents neither a desirable nor an undesirable location. All intermediate colors such as yellow-green can represent an intermediate level of desirability such as "less desirable" (compared to "desirable"). Further, weighting coefficients and functions such as thresholding and leveling may be applied to the different types of electrophysiological data, such that the contribution of each type of electrophysiological data to a summarized graphical depiction can be enhanced, diminished or removed with respect to the other types of electrophysiological data. In particular, dynamic changing of the contribution of each type of electrophysiological data allows the user to study each type of electrophysiological data regarding its affect on the final treatment decision (e.g., some types of electrophysiological data may produce discrepancies and the user decides on how to interpret and handle these discrepancies).

According to one aspect of the invention, there is provided a system and method for graphically depicting a desired region for a treatment instrument with respect to a patient, characterized in that different types of electrophysiological data of the patient, which were previously acquired, are combined to provide a graphical depiction that indicates the desired region for the treatment instrument.

More particularly, the different types of electrophysiological data are normalized and, more particularly, that data is interpolated and/or extrapolated such that data within each of the different types of electrophysiological data corresponds to one another.

Yet more particularly, each of the different types of electrophysiological data are color coded based on at least two colors, wherein a first color represents desirability and a second color represents undesirability and, more particularly, at least one additional color that represents neither completely desirable nor completely undesirable. The colors can represent qualitative and quantitative meanings with respect to a clinical treatment success of the placing the treatment instrument in the desired region.

More particularly, the different types of electrophysiological data include numeric data, binary data, textual data, graphical data, acoustical data, or any combination thereof.

More particularly, interactively changeable weighting coefficients as well as functions such as thresholding or leveling can be applied to each of the different types of electrophysiological data, wherein each weighting coefficient as well as the functions affect the respective electrophysiological data's contribution to the combined graphical depiction.

More particularly, the graphical depiction is overlaid to anatomical image data of the patient and, yet more particularly, the graphical depiction is overlaid to a two-dimensional or a three-dimensional pattern of the anatomical image data.

According to another aspect of the invention, there is provided a system for graphically depicting a desired region for a treatment instrument with respect to a patient, including a data acquisition module, wherein the data acquisition module receives as an input different types of electrophysiological data of the patient, a storage medium for storing the different types of electrophysiological data, and a data visualization module, wherein the data visualization module retrieves each of the different types of electrophysiological data from the storage medium and generates a graphical depiction that indicates the desired region for the treatment instrument.

More particularly, the data visualization module includes a summarization control circuit, the summarization control circuit applying a weighting coefficient and/or a function such as thresholding or leveling to each of the different types of electrophysiological data.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed.

DETAILED DESCRIPTION

In the detailed description that follows, corresponding components have been given the same reference numerals, regardless of whether they are shown in different embodiments of the present invention. To illustrate the present invention in a clear and concise manner, the drawings may not necessarily be to scale.

The present invention relates to a system and method for graphically depicting a desired region for a treatment instrument with respect to a patient. According to the present invention, electrophysiological data is acquired and viewed intra-operatively during human brain surgery to identify an optimum implantation position of a stimulation electrode as well as post-operatively to review clinical results. The acquired electrophysiological data can be primarily categorized as microelectrode recording and stimulation (MER/S) data containing numeric values (e.g., stereotactic position, stimulation threshold, efficiency), binary (e.g., yes/no, rhythmic/non-rhythmic), textual information (e.g., comments, stimulation effect name), iconic or graphical information (e.g., snapshot bitmaps of the signal recording, iconized effect descriptions), acoustical information(e.g., noise samples of the signal recording), or any other type of information that describes the MER/S data.

The graphical depiction is based on the different types of MER/S data of the patient. In accordance with the invention, the different types of MER/S data are combined to produce a simple yet meaningful graphical depiction that can be used to quickly and easily convey a desired target region within the patient.

The graphical depiction can utilize a simple color coding scheme, wherein a 100% desirable result is shown in a first color, e.g., green, and a 100% undesirable result is shown in a second color, e.g., red. One or more additional colors may be used to indicate partially desirable/undesirable results, e.g., yellow may indicate a region that is neither desirable nor undesirable. According to one embodiment, colors that are given by a continuous spectrum are chosen.

The graphical depiction can be controlled via weighting coefficients as well as via color changing functions such as thresholding or leveling, which are applied to each of the different types of MER/S data, thereby permitting certain data to be interactively emphasized or de-emphasized with respect to other data. In particular, the ability to interactively change the parameters for the combined graphical representation allows the affect of each type of MER/S data to be studied with respect to its meaning or reliability for the clinical decision. Additionally, the graphical depiction can be provided in a two-dimensional patterned graph or overlaid with a two-dimensional or three-dimensional anatomical image of the patient.

Figure 1:
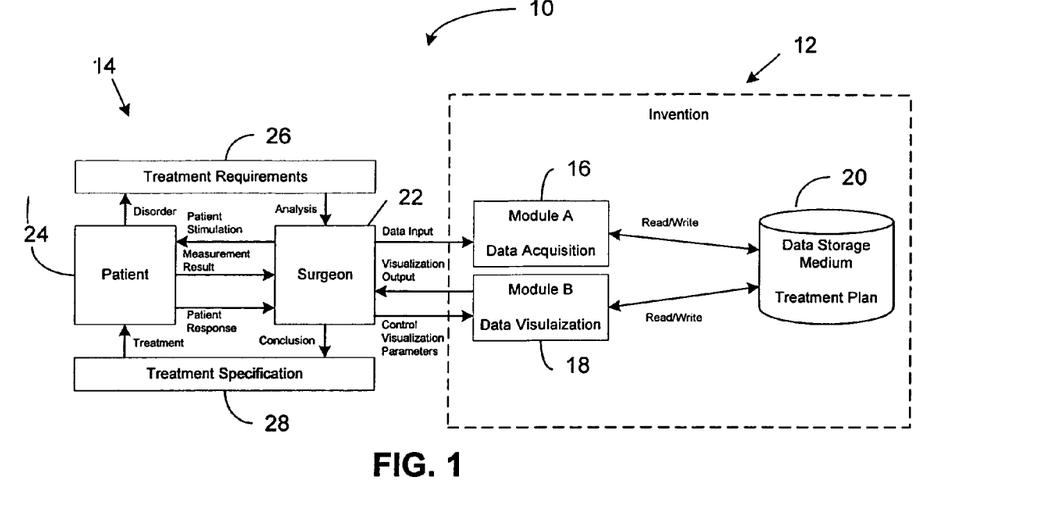
FIG. 1 is a block diagram illustrating the present invention and its interaction with a surgeon.

The above features of the present invention will now be described with respect to the drawings. Referring initially to FIG. 1, there is provided a block diagram 10 illustrating a system 12 according to the present invention in relation to a treatment process 14. The system. 12 includes a data acquisition module 16, a data visualization module 18 and a storage medium 20. The treatment process 14 illustrates a surgeon 22 interacting with a patient 24, wherein based on treatment requirements 26, a treatment specification 28 is formulated by the surgeon 22.

In treating Parkinson's disease with deep brain stimulation (DBS), for example, the surgeon 22 may collect MER/S data of the patient 24, wherein first, a microelectrode is used for recording neuronal cell signals from regions of the patient's brain, and second, periodic electrical stimulation signals having a specified strength and shape are injected via a stimulation electrode into regions of the patient's brain.

The results of microrecording (neuronal cell signals) are observed, measured and evaluated by the surgeon 22, who then enters the data directly into the data acquisition module 16 (or into an intermediate storage media, e.g., paper protocol, before entering the data into the system). In evaluating the data, the surgeon may consider the firing rate, detection of certain brain area activity, pattern analysis, or any other parameter that can be used to determine optimum DBS stimulation microelectrode placement.

The results of the stimulation (patient response and corresponding stimulation parameters) are observed, measured and evaluated by the surgeon 22, who then enters the data directly into the data acquisition module 16 (or into an intermediate storage media before entering it into the system). In evaluating the data, the surgeon may consider desired stimulation effects such as tremor, rigor or akenesia improvement as well as undesired side-effects such as parasthesia, numbness, speech problems, etc. The data acquisition module 16 subsequently stores the data on the storage medium 20. The entered data can include measured results, patient responses, stimulation parameters, etc., according to a specific patient disorder, as well as a proposed treatment as ascertained by the surgeon 22.

The data visualization module 18, in accordance with the invention, generates a controlled graphical depiction of a desired location for the treatment instrument. As will be described in more detail below, the graphical depiction is generated from a plurality of different types of MER/S data to produce a simple yet informative presentation for a desired location of the treatment instrument. Additionally, the surgeon may interactively control the graphical depiction by altering control parameters, e.g., weighting coefficients or color changing functions such as thresholding or leveling, for each type of MER/S data. The weighting coefficients, for example, can be altered via the data visualization module 18 using an interface (e.g., a slider or the like). Based on the graphical depiction, the surgeon 22 determines a location within patient's brain wherein the stimulation microelectrode provides a desired result. Additionally, the surgeon 22 determines the clinical meaning (decisive relevance, discrepancy, etc.) of each different type of MER/S data by dynamically altering the weighting and/or color functions.

It will be appreciated that while the invention is described with respect to a surgeon entering data, the data can be entered by personnel other than a surgeon, e.g., a nurse or the like, or via automatic entry, e.g., the MER/S data is analyzed via a computer and entered into the data acquisition module 24. As will be discussed in more detail below, data can be entered using various data entry mechanisms, including a keyboard, mouse, touchscreen, etc., or via voice or video recognition.

Figure 2:
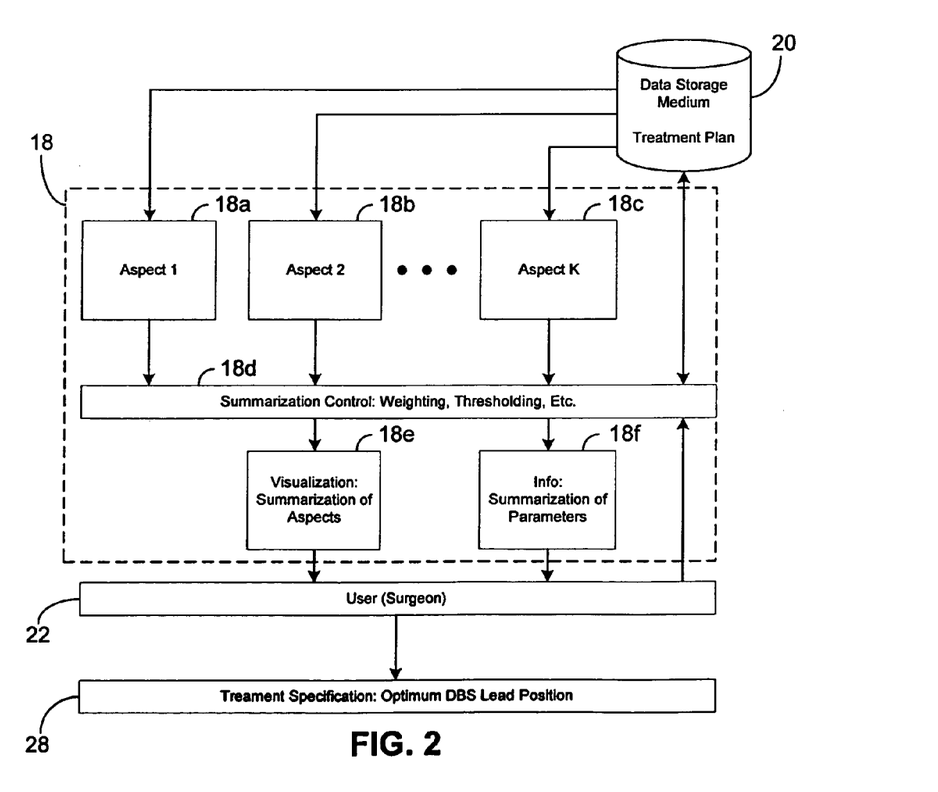
FIG. 2 is a block diagram providing further detail of the data visualization module of FIG. 1.

FIG. 2 provides additional detail of the data visualization module 18. As can be seen, the data visualization module 18 retrieves from the storage medium 20 each of the different types of MER/S data 18a, 18b and 18c. The MER/S data can be in various forms, e.g., numeric, binary, textual, iconic, acoustical, etc.) and can include measured results, patient responses, stimulation parameters, etc., according to a specific patient disorder, as well as a proposed treatment as ascertained by the surgeon. Examples of MER/S data are shown below:

a) improvement of tremor with 100% efficiency achieved at a threshold current of 1.2 mA at center track, 5 mm above target;

b) speech problem with 75% severity achieved at a threshold current of 3.0 mA at center track, 5 mm above target; and c) position, qualified to be 50% optimal based on recording high irregular activity at center track, 7 mm above target.

Each of the different types of MER/S data are provided to a summarization control circuit 18d of the visualization module 18. The summarization control circuit 18d performs weighting, thresholding and/or leveling of the data, and the user defined settings (combined visualization parameters) can be stored to the data storage medium. Weighting pertains to applying weighting coefficients to each of the different types of MER/S data, while thresholding is used to change the color distribution (e.g., thresholding colors "below" yellow-green are displayed as red, colors "above" and equal to yellow-green are displayed green) within a graphical representation of one specific type of MER/S data. In other words, based on whether or not the data is more desirable or less desirable, the data is color coded so as to indicate either desirable (green) or undesirable (red) without showing an intermediate color range. Leveling refers to introducing a non-linearity with respect to one measured aspect before it is weighted.

The weighting coefficients permit the controlled display of the graphical depiction, such that certain data may have more or less influence on the final graphical depiction than other data. Thresholding or leveling, on the other hand, provides the surgeon the ability to graphically blend out doubtful or irrelevant information brought by specific type of MER/S data, such as very low desirable or undesirable stimulation results.

Weighting coefficients may be used to emphasize, diminish or remove the effect of a particular type of MER/S data. For example, a particular type of MER/S data may be deemed less reliable than other types of MER/S data. Using the weighting coefficients, the less reliable data type can be reduced or minimized such that its influence on the graphical depiction generated by the data visualization module 18 is diminished, or even removed completely (e.g., the weighting coefficient for the particular parameter is set to 0%). Weighting also can be used to study the influence of a particular type of MER/S data on the decision which would be based on the combined graphical representation (e.g., if only one of the many different types of MER/S data causes discrepancy about an optimum position, this data can be removed or down-weighted accordingly to reflect the basis for the decision).

Thresholding, for example, is useful when the surgeon has acquired a large amount of data for one specific aspect, but he only wants to graphically consider a specific sub-part of one measured aspect (e.g., only tremor improvement results of more than 75% should be taken into account for the summarization graph).

Leveling, for example, is useful when the surgeon desires to bring a non-linearity into one specific measured aspect before that aspect is weighted against other aspects (e.g., a 100% speech problem is 4-times worse than a 50% speech problem, and not only 2-times worse as the entered percentage value from MER/S data acquisition would indicate).

It is noted that the summarization control circuit 18d is not limited to weighting, thresholding, and leveling of the data. The summarization control circuit 18d can include other methods for graphically processing the image so as to enhance the image or to make the information conveyed by the image more meaningful to the surgeon.

The output of the summarization control circuit 18d is provided to a visualization circuit 18e and to an information circuit 18f. The visualization circuit 18e combines the different types of MER/S data to generate a graphical depiction of a desired region for the treatment instrument. Preferably, the visualization circuit 18e utilizes three colors to generate the graphical depiction, although more or fewer colors may be used. The colors represent qualitative and quantitative meanings with respect to the clinical treatment success of the proposed implantation region and stimulation signal.

For example, each of the different types of MER/S data may indicate areas or regions within the brain that provide completely desirable results (e.g., 100% good, 100% efficient, 100% positive, etc.) or completely undesirable results (e.g., 100% bad, 100% severe, 100% undesired, 100% negative, etc.). Other regions may provide neither desirable nor undesirable results (e.g., 50% good, 50% efficient, 50% positive, etc.). The completely desirable results may be depicted using a first color, such as green, while the completely undesirable results may depicted using a second color, such as red. The visualization circuit 18e combines each of the different types of MER/S data so as to create a single graphical depiction of all the data. As the different types of MERIS data are combined, areas or regions that have the same color maintain that same color, e.g., green plus green is green, red plus red is red, yellow plus yellow is yellow. On the other hand, areas or regions that have different colors are given a different color, e.g., red plus green is yellow.

Further, additional colors may be used to provide an indication of the level of agreement or disagreement between the different types of MER/S data. For example, areas or regions that have predominantly undesirable results but with some desirable results may be shown as light red (e.g., 75% undesirable may be displayed as light red). Similarly, areas or regions that have predominantly desirable results but with some undesirable results may be shown in light green (e.g., 75% desirable may be displayed as light green). According to one embodiment, colors that are given by a continuous spectrum such as that derived from common color definitions (hue/saturation/brightness), are chosen (e.g., green [120°/100%/100%], light green [900/100%/100%], yellow [60°/100%/100%], light red [300/100%/100%], red [0°/100%/100%]). The color coding can be used for each of the different types of MER/S data in order to provide a summarized and patterned visualization of all MER/S data together in one (mixed) graphical depiction.

Moving now to the information circuit 18f, this circuit simply summarizes the combination parameters applied to the graphical representation in order to inform the surgeon 22 about which types of MER/S data have been considered and in which way they have been considered (e.g., a legend of the graph could indicate: the graph considers "tremor improvement" and "numbness" by 1:1). This is facilitates interpretation of the graphical depiction since all types of MER/S data are displayed in a highly compressed, color-coded and combined graphical representation and sufficient information about the graphical combination is required for safe and effective use of the data. This data, along with the graphical depiction, are provided to the surgeon 22 who then uses the data along with his own experience to formulate a treatment specification 28.

As was noted above, the graphical depiction generated in accordance with the present invention is derived from a plurality of graphical depictions of different types of MER/S data. Generation of the single graphical depiction from the plurality of graphical depictions will now be discussed using three exemplary types of MER/S data: tremor improvement, burstic activity, and parasthesia. While only three types of MER/S data are utilized in the present example, it should be appreciated that more or fewer types of MER/S data may utilized as required during individual patient treatment.

In describing the present invention, it is noted that only a single axis "dz" corresponding to a depth of implantation will be used to describe the position of the electrodes. It will be appreciated by those skilled in the art, however, that in addition to a depth or "dz" component, "dx" and "dy" components also are utilized to position the electrode.

Figure 3:
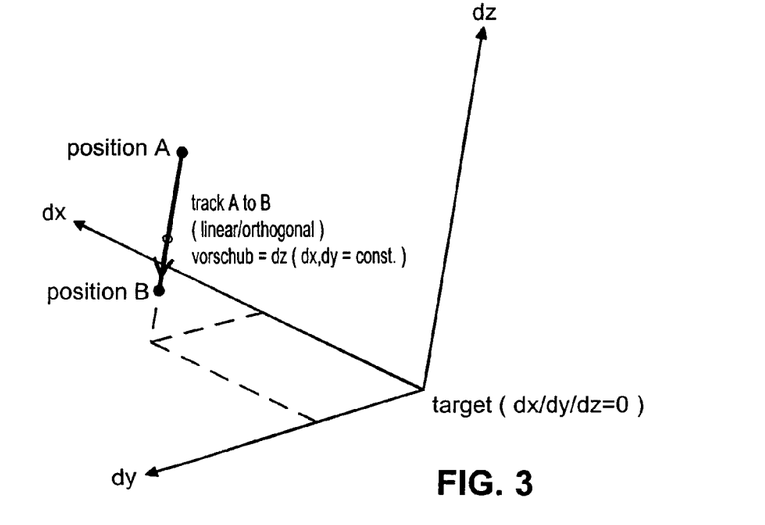
FIG. 3 defines a three-dimensional volumetric space for positioning a microelectrode.

Referring briefly to FIG. 3, the volumetric space (dx, dy, dz) in which the MER/S data is measured is shown. The measurement electrode is positioned by varying the depth (dz) along a linear track (from position A to position B) and by varying the track (dx, dy) itself by changing an angle and radius, which can be adjusted correspondingly on a micropositioning system. Thus, the actual position of the measurement electrode depends on dx, dy and dz. Use of dx and dy is omitted from the following examples to simplify the description of the invention. The components dx and dy, however, are implied in the following examples.

Figure 4A:
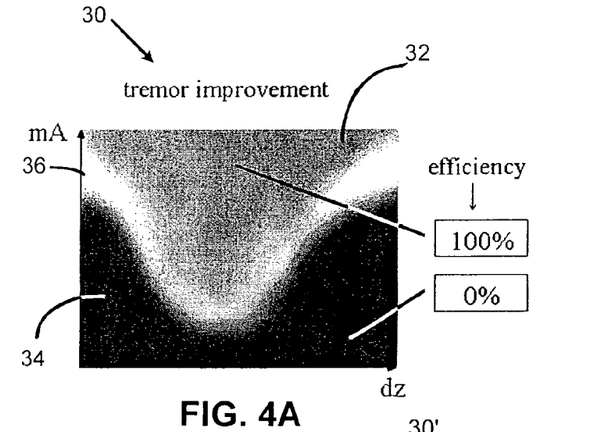
FIG. 4A is a graphical depiction of a first type of electrophysiological data relating to tremor reduction in a patient.

Moving to FIG. 4A, an exemplary graphical depiction 30 for a first type of observed MER/S data of the patient 24 is shown. The data pertains to a reduction in the patient's tremors (tremor improvement) as the depth (dz) and stimulation current (mA) applied to the patient 24 are varied. The graphical depiction 30 includes a first region 32 that represents a desirable effect (e.g., a reduction in tremors) and is given a first color (e.g., green), a second region 34 that represents an undesirable effect (e.g., no reduction in tremors) and is given a second color (e.g., red), and a third region 36 that represents neither desirable nor undesirable effect (e.g., some reduction in tremors) and is given a third color (e.g., yellow).

The first region 32 of the graphical depiction 30 is a region in which the efficiency of the effect is 100%. In other words, by applying stimulation to the patient, the amount and/or severity of the tremors is improved by 100%. The second region 34 is a region in which the effect is 0% (e.g., sufficient stimulation was not applied to the patient and thus no change in the amount or severity of the tremors was observed). Between the two regions is a region where the efficiency transitions from 0% to 100%. As will be appreciated by those skilled in the art, the effect of the stimulation depends on the location within the brain that the stimulation is applied as well as the strength of the stimulation.

Figure 4B:
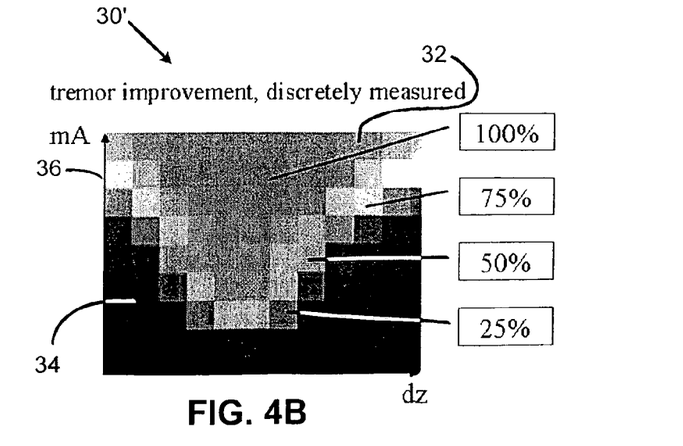
FIG. 4B is a discrete representation of the graphical depiction of FIG. 4A.

Theoretically, there will be one specific location (dz) on the patient where a desired effect (e.g., tremor reduction) will appear by applying a minimum stimulation current (mA). This location would be the preferred location for placing the implantation microelectrode, considering the only aim is to reduce tremors. However, due to real case clinical conditions (e.g., time constraints, limited patient cooperation, etc.) and technological limitations (e.g., discrete measurements, etc.), the measurement of this "theoretical reality" will be affected by significant discretion. The graphical depiction of this "theoretical reality" would appear as shown in FIG. 4B, wherein discrete regions can be identified in the graphical depiction 30'.

Figure 5:
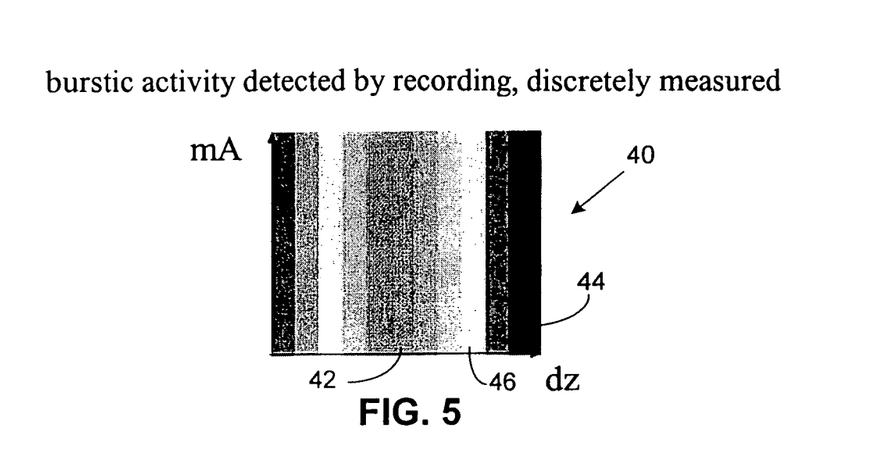
FIG. 5 is a graphical depiction of another type of electrophysiological data relating to burstic activity in the patient's brain.

FIG. 5 illustrates the above color concept applied a second type of MER/S data, namely burstic activity 40 measured within the brain. Burstic activity is a very dense sequence of spikes that correspond to specific neuronal activity. By searching for bursts within the brain, it is possible to distinguish functional brain areas from one another. The graphical depiction 40 can be used to identify or mark specific depth positions (dz) within the patient that correspond to a specific measured microelectrode recording result (e.g., whether or not burstic activity was detected by the microelectrode).

Since burstic activity may be an indicator that the microelectrode is in a desirable location in the brain, high rates of burstic activity can be defined as desirable, no burstic activity can be defined as undesirable, and some burstic activity can be defined as neither desirable nor undesirable. The color-coding utilized in the graphical depiction 30 of FIG. 4A also is used with the graphical depiction 40 of FIG. 5. More specifically, regions 42 that exhibit high burstic activity are deemed to be desirable and are shown in a first color (e.g., green), regions 44 that exhibit no burstic activity are deemed undesirable and are shown in a second color (e.g., red). Regions 46 that exhibit some burstic activity, but not enough to be deemed to be desirable are shown in a third color (e.g., yellow). As can be seen in FIG. 5, high burstic activity is recorded for implantations at medium depths (dz), while no burstic activity is recorded for implantations at large and shallow depths (dz).

It is noted that the graphical depiction 40 illustrates the use of additional intermediate regions for burstic activity (i.e., regions having additional colors to illustrate a degree of desirability or undesirability). Such additional regions are merely exemplary and are not discussed for sake of brevity.

As can be seen in FIG. 5, burstic activity is described with respect to implantation depth (dz) as well as stimulation current (mA). While this does not make sense from a scientific point of view (the stimulation current is not assigned to any parameter of the microrecording data), the graphical depiction of FIG. 5 is valid for showing that burstic activity varies along a depth (dz) while not varying along the axis of stimulation current (mA).

Figure 6:
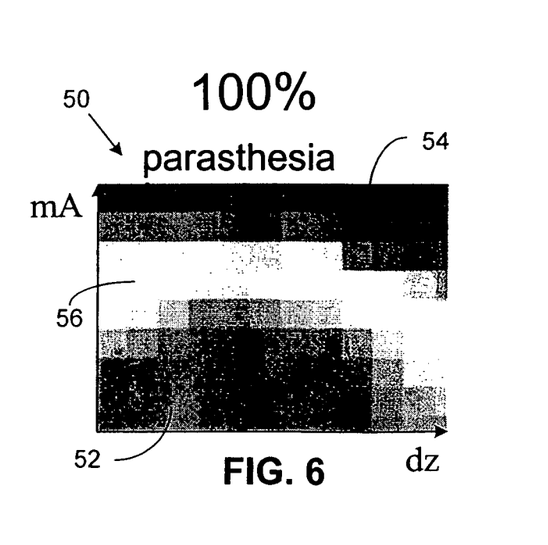
FIG. 6 is a graphical depiction of yet another type of electrophysiological data relating to parasthesia of the patient.

FIG. 6 illustrates the above described color concept applied to a third type of MER/S data, namely parasthesia 50. For example, certain levels of stimulation (and/or locations of stimulation) may produce undesirable side effects, such as numbness, tingling, etc. These side effects may occur based on the specific location in the brain that the stimulation was applied or on the strength of the stimulation. Levels of stimulation and/or regions of the brain that produce no parasthesia are identified as regions 52 providing a desirable result (e.g., shown in green), while levels of a stimulation and/or regions of the brain that produce significant parasthesia are identified as regions 54 providing an undesirable result (e.g., shown in red). Levels of stimulation and or regions of stimulation that provide minor parasthesia are identified as regions 56 providing neither desirable nor undesirable results (e.g., shown in yellow).

As can be seen in FIG. 6, high levels of parasthesia are experienced for relatively high levels of stimulation current and for relatively deep implantation of the electrode within the brain. As the relative level of stimulation and the depth of the implant are reduced, the parasthesia diminishes until no parasthesia is observed for relatively low stimulation levels and relatively low to moderate implantation depths.

The above described visualizations or graphical depictions of the three types of MER/S data are a preparative step which is used to realize a mixed-display MER/S graphical depiction concept according to the present invention, as will be described below.

Figure 7:
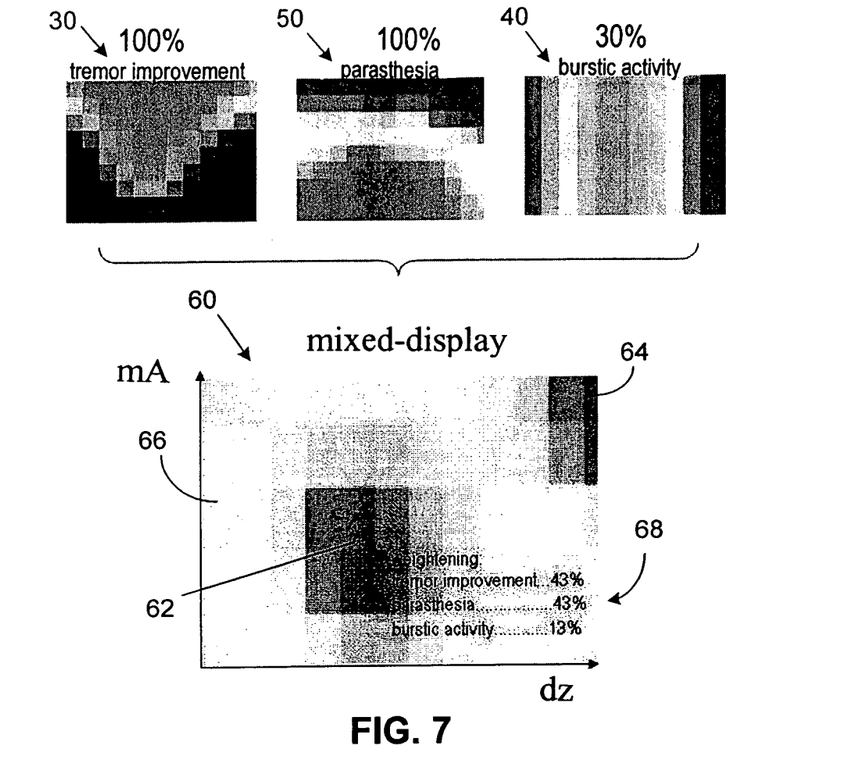
FIG. 7 is a mixed graphical depiction derived from the combination of the graphical depictions of FIGS. 4-6 in accordance with an embodiment of the invention.

Moving to FIG. 7, a mixed display or summarization 60 in accordance with the present invention is constructed from each of the individual graphical depictions 30, 40 and 50. More specifically, the graphical depictions 30, 40 and 50 are combined as layers and normalized to form the single graphical depiction that represents a summarization 60 of all MER/S data obtained of the patient.

Normalizing the graphical depictions, as used herein, refers to using implicit, explicit, interpolated as well as extrapolated data. For example, each of the different graphical depictions should embrace (without gap) the same depth-axis and threshold-axis range in order to process all the data into a single graphical depiction. Due to various considerations (e.g., not all stimulation effects have been measured at all depth positions, recording results have been measured at different depth positions than the stimulation results, etc.), data obtained from one type of MER/S data may not precisely correspond to data found in another type of MER/S data. As a result, a first MER/S graphical depiction (e.g., the tremor graphical depiction 30 of FIG. 4A) may include data for a specific stimulation current and implantation depth, while a second graphical depiction (e.g., the parasthesia graphical depiction 50 of FIG. 6) may not include data for the same specific stimulation current and implantation depth. To compensate for the missing data, interpolation and/or extrapolation is performed on the data to arrive at an approximation of the data for the missing point or points. Other defined/specific data processing measures (e.g., calculating supporting-points from sampling-points) also may be implemented to approximate the missing data.

Moving back to the summarization 60, the colors displayed in the summarization 60 correspond to the colors of each of the individual graphical depictions 30, 40 and 50. For example, if each of the individual graphical depictions 30, 40 and 50 indicate undesirable results for a first region (e.g., high stimulation and deep implantation), the summarization 60 also will indicate undesirable results for the first region. Similarly, if each of the individual graphical depictions 30, 40 and 50 indicate desirable results for a second region (e.g., medium stimulation and medium implantation), the summarization also will indicate desirable results for the second region. However, where there is disagreement between the individual depictions, then the summarization 60 is constructed such that the region is identified as neither desirable nor undesirable. In other words, the color coding for the summarization 60 can be described as "red"+"red"="red", "green"+"green"="green", "yellow"+"yellow"="yellow", "red"+"green"="yellow", "yellow"+"green"="light green", etc., wherein the addends correspond to the individual graphical depictions 30, 40 and 50, and the result or "summation" refers to the color used in the summarization 60 for that particular region. As will be appreciated, additional colors may be implemented to reflect varying degrees of desirability for particular regions.

As can be seen in FIG. 7, the combination of the different types of data yields a summarization 60 that indicates a desirable result is obtained near a center region 62, e.g., at a medium depth and stimulation current. Undesirable results are obtained for a region 64 that identifies relatively deep implantations having relatively high stimulation current, while the remainder 66 of the summarization 60 illustrates neither desirable nor undesirable results. Accordingly, the exemplary summarization 60 indicates that a preferred location for the treatment instrument is at a medium depth, and that a medium stimulation signal is injected at the medium depth.

The summarization 60 can be further controlled by dedicated weighting factors as well as MER/S data type related functions such as thresholding, leveling, etc., which allow certain data to be emphasized or de-emphasized with respect to other data. In doing so, the user can interactively study the impact of the chosen aspect on his or her potential decision regarding a final optimum position of the DBS implantation microelectrode. Weighting factors, for example, can be implemented using a slider on a user interface (not shown) or by direct numerical entry, e.g., entering a numerical weighting factor for each type of data (not shown). The weighting factors, which can be displayed as a legend 68 next to or on the summarization 60, communicate to the surgeon which aspects of MER/S data have been considered and the relative influence of the respective data.

In normal clinical conditions, one or more desired effects as well as one or more undesired effects will be measured during MER/S data acquisition. In such cases, the patterned visualization according to the present invention will show at least one of a region 62 providing a desired result, a region 64 providing an undesired result or a region 66 providing an indifferent result. As discussed previously, these regions may be identified by the colors green (desired) red (undesired) and yellow (neither desired nor undesired). Additionally, other intermediate colors may be used to identify relative levels of desirability. The resulting regions (desired 62, undesired 64, and indifferent 66) can be used to easily locate the optimum location for an implantation electrode and/or to identify an optimum stimulation signal.

In determining the optimum location of the implantation electrode, and as was noted above, a simple and intuitive rule should be kept in mind when looking at the visualization according to the present invention. That is, the optimum depth position (dz) for an implantation electrode is where: 1) a minimum current can be found for transitioning between an undesired region (e.g., red or yellow); and 2) a maximum current can be found for transitioning from a desired region (e.g., green) to an undesired region (e.g., red).

Figure 8:
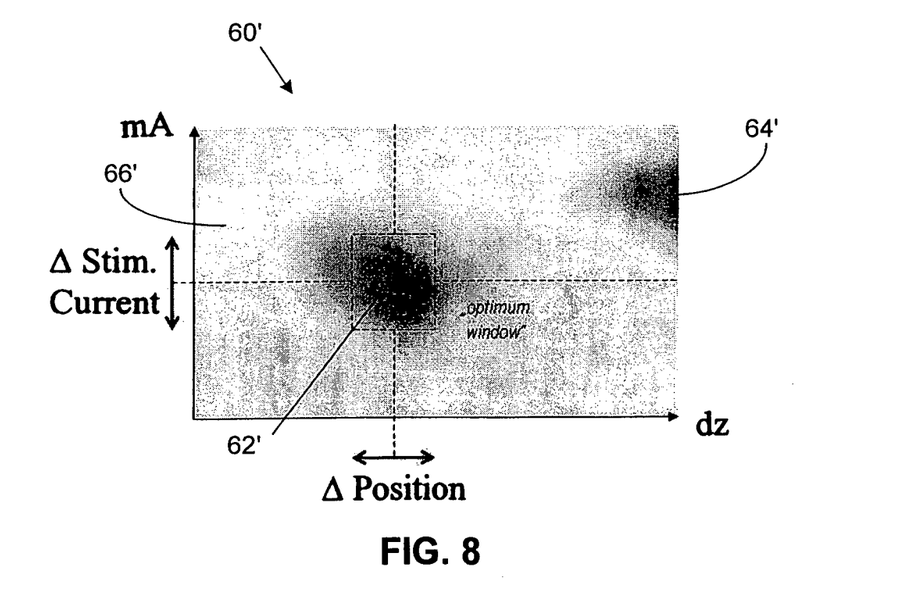
FIG. 8 illustrates the graphical depiction of FIG. 7 after graphical smoothing methods have been applied (such as interpolation and extrapolation) in accordance with an embodiment of the invention.

Additionally, and with further reference to FIG. 8, filtering, interpolation and extrapolation techniques can be used to further enhance the quality of the graphical depiction. Such techniques can lead to a smoother appearance in the graphical depiction, particularly along the transition points between the different regions. The shape of the region 62' identifying a desired result provides a qualitative and quantitative perspective of a safety margin, effectiveness and/or potential risk for placing the implantation electrode. For example, if the shape of the region 62' is broad along the depth axis (dz), inaccurate implantation still can lead to acceptable clinical results. If the shape of the region 62' extends along the current axis, then there is what is known as a "current puffer", wherein a lower occurrence of negative side effects can be expected as the stimulation amplitude (e.g., current) may need to be increased due to inaccurate implantation of the electrode during the post-operative patient care and device adjustments.

The graphical summarizations 60 and 60' according to the present invention allow a surgeon to view intra-operatively and post-operatively all aspects of the MER/S data either separately (e.g., by setting one weighting coefficient to 100% and all other weighting coefficients to 0%) or in a summarization (e.g., by setting all weighting coefficients >0%). In doing so, the surgeon is provided with a clear visualization of all the data which can be used in the decision making process for implanting the electrode.

Further, the present invention can be displayed as a two-dimensional patterned graph or as an overlaid pattern displayed in two-dimensions or three-dimensions in correlation with the patient's anatomy. For example, the MER/S data can be visualized overlaid to two-dimensional or three-dimensional magnetic resonance images of the patient's brain. By controlling non-visualizable dimensions of the summarization 60 (e.g., the stimulation current axis) via an additional user interface (e.g., a slider) in a computerized system, all measured MER/S data can be visualized together as an overlay to the patient's anatomy. This permits the correlation of magnetic resonance imaged patient anatomy with MER/S data acquired intra-operatively. As will be appreciated, imaging techniques other than magnetic resonance imaging may be used in conjunction with the present invention including, for example, computer tomography (CT), ultrasound, x-ray, or other known imaging techniques.

Figure 9A:
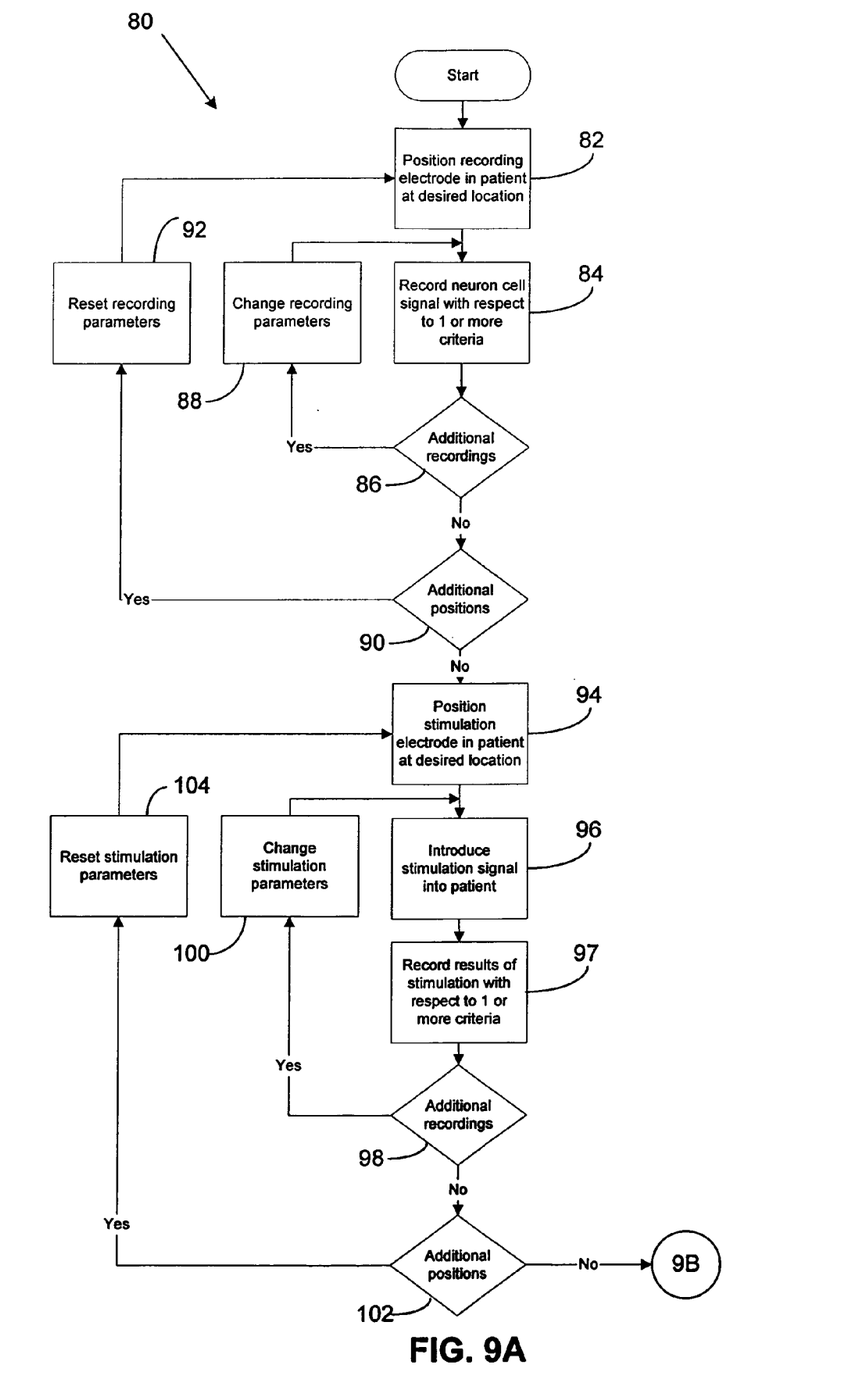
FIG. 9A is a flow diagram illustrating the steps for carrying out a method for graphically depicting a desired region for a treatment instrument with respect to a patient in accordance with an embodiment of the invention.
Figure 9B:
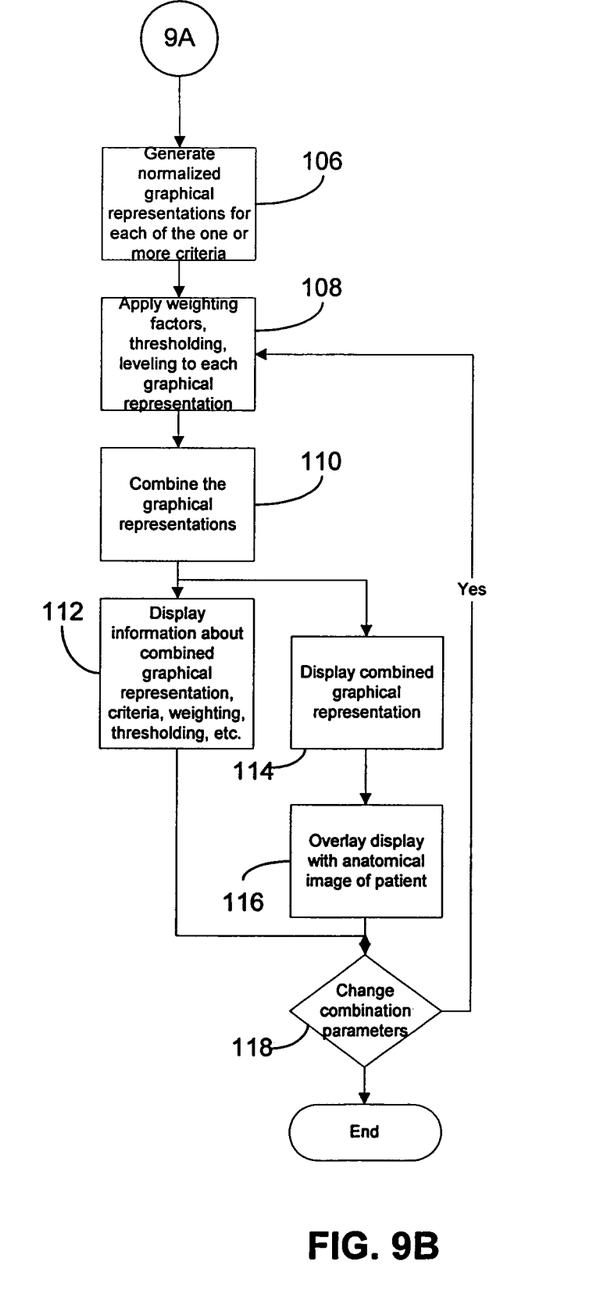
FIG. 9B is a continuation of the flow diagram of FIG. 9A.

Moving now to FIGS. 9A and 9B, a flow diagram 80 illustrating the method of graphically depicting a desired region for a treatment instrument with respect to a patient is shown. The flow diagram includes a number of process blocks arranged in a particular order. As should be appreciated, many alternatives and equivalents to the illustrated steps may exist and such alternatives and equivalents are intended to fall with the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

Beginning at step 82, a recording electrode is positioned in the patient at a desired location, and at step 84 neuron cell signals with respect to one or more types of MER/S data are recorded. The signals recorded from the patient are the electrical signals of the patient's brain at the functional area where the measurement microelectrode is placed. An external voltage or current stimulation signal is not applied at this time. However, a passive signal, such as a light signal directed into the patient's eyes or movement of the patient's arms or legs, may be introduced. If increased neuronal activity appears in conjunction with the passive stimulation signal, this activity can be documented as a recording result.

Next at step 86 it is determined whether additional recordings will be obtained. If additional recordings are desired, then at step 88 the recording parameters are changed and the method moves back to step 84. If additional recordings are not desired, then at step 90 it is determined whether additional recording positions are desired. If additional positions are desired, then at step 92 the recording parameters are reset and the method moves back to step 82, wherein the recording electrode is repositioned in the patient.

If additional recording positions are not desired, then at step 94 a stimulation electrode is positioned in the patient at a desired location, and at step 96 a stimulation signal (e.g., current or voltage signal) having a predetermine magnitude and shape is introduced into the patient. At step 97, the results of the stimulation signal are recorded with respect to one or more criteria (e.g., one or more different types of MER/S data). It is noted that during this recording step, no neuronal cell recording is done for measuring the stimulation result. The measured result is the effect of the stimulation signal on the patient. In other words, the surgeon is working on and with the patient, e.g., holding the patient's arms to determine the degree of rigor improvement while the stimulation signal is changed as well as switched on and off. The surgeon himself will measure and record the efficiency of all appearing desired effects (e.g., rigor improvement) and/or the severity of all undesired effects (e.g., numbness).

Next at step 98 it is determined whether additional recordings will be taken. If additional recordings are desired, then at step 100 the stimulation parameters are changed (e.g., the magnitude of the stimulation signal, shape, period, etc. are changed) and the method moves back to step 96. If additional recordings are not desired, then at step 102 it is determined whether stimulation of additional positions in the patient are desired. If additional positions are desired, then at step 104 the stimulation parameters are reset and the method moves back to step 94, wherein the stimulation electrode is moved to a new position in the patient.

If additional positions for the stimulation electrode are not desired, then at step 106 normalized graphical representations for each of the different types of MER/S data are generated. Normalizing the data includes setting all graphical representations to the same scale and range (the minimum and maximum depth, the minimum and maximum threshold, etc.). Depending on the acquired data, it may be necessary to interpolate or extrapolate data for one or more types of MER/S data as described previously.

As was discussed above, the graphical depictions 30, 40 and 50 for each of the different types of MER/S data are constructed based on a color coding scheme, wherein a first color (e.g., green) represents a desirable result, a second color (e.g., red) represents an undesirable result, and a third color (e.g., yellow) represents neither a desirable nor an undesirable result. Further, more or fewer colors may be used based on the level of detail desired in the graphical depictions.

Next at step 108, weighting coefficients, thresholding and/or leveling are applied to each of the individual graphical representations. The weighting coefficients, thresholding and leveling allow the surgeon to control the influence that each type of MER/S data has on the combined graphical depiction. At step 110, the individual graphical representations for each of the different types of MER/S data are combined to form the overall graphical summarization. In combining the different graphical depictions, regions that have the same color will maintain the same color, while regions that have different colors will be given the third color (e.g., yellow). For example, regions in the individual graphical depictions that have all red or all green will maintain red or green in the summarization. Regions that have different colors (e.g., red+green, yellow+red, yellow+green), however, will be shown in a corresponding mixed color (e.g., yellow, light red, light green, etc.). Thus, the summarization 60 will identify those regions that are completely desirable, completely undesirable and neither desirable nor undesirable.

At steps 112 and 114, the graphical depiction and information on the graphical depiction are displayed for the surgeon to view. The information on the graphical depiction can include the relative weighting factors, the amount of thresholding or leveling applied to specific types of data, etc. At step 116, the graphical depiction can be optionally overlaid with an anatomical image of the patient. This can be a two-dimensional or a three-dimensional anatomical image, for example. The anatomical image may be a magnetic resonance image of the patient's brain, for example, wherein the graphical depiction identifies regions of the brain by color. More specifically, regions of the brain wherein implantation provides desirable results may be shown in green, regions that provide undesirable results may be shown in red, and regions that provide neither desirable nor undesirable results may be shown in yellow. At step 118, the surgeon may decide to dynamically adjust the combination parameters or to accept the graphical depiction as is. If the surgeon deiceds to adjust the parameters, the method moves back to step 108 and repeats steps 108 through 118 with the new parameters.

Figure 10A:
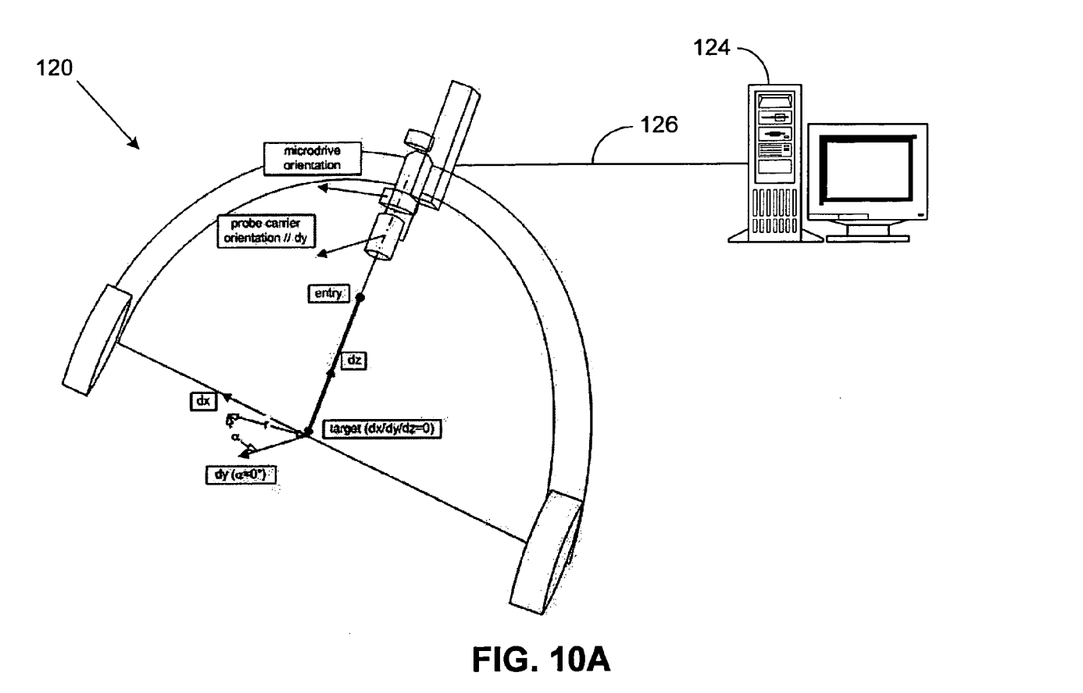
FIG. 10A is a perspective view of a stereotactic arc system that can be used in conjunction with the present invention.
Figure 10B:
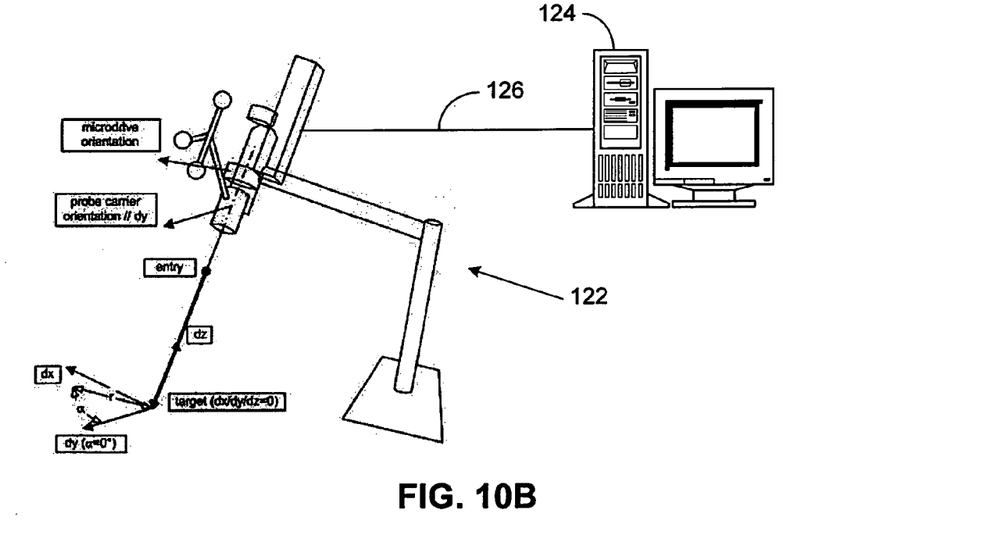
FIG. 10B is a perspective view of a frameless holding arm system that can be used in conjunction with the present invention.

Moving now to FIGS. 10A and 10B, systems for positioning the microelectrode will be briefly described. As was discussed above, MER/S data is measured via electrodes positioned within the patient's brain. A dedicated configuration of electromechanical devices generally is used to accurately position and rigidly hold the microelectrode as well as the stimulation microelectrode during MER/S data acquisition. In most cases, a stereotactic arc system or any other comparable type of positioning device (e.g., a frameless holding arm) is used to position the microelectrodes.

FIG. 10A illustrates an exemplary stereotactic arc system 120, while FIG. 10B illustrates a frameless holding arm system 122. Both positioning systems 120 and 122 are communicatively coupled to a computer system 124 via a communication link 126, e.g., an Ethernet connection, a proprietary network, manual data transfer, or the like. The computer system 124 controls the operation of the positioning systems 120 and 122 such that the location of the microelectrode is precisely known and maintained. Additionally, the computer system 124 can regulate the period and magnitude of the stimulation signal applied to the patient's brain. Stereotactic arc systems and frameless holding arm systems are well known in the art and, therefore, further discussion with respect to such systems is omitted for sake of brevity.

The above described methodology can be implemented by a computer program which, when it is executed by computer system 124 or by a separate computer (not shown), performs one or more of the method steps described above. The computer system 124, in conjunction with the positioning systems 120 and 122, allows the surgeon to identify and position the microelectrodes to achieve a desired effect.

Figure 11:
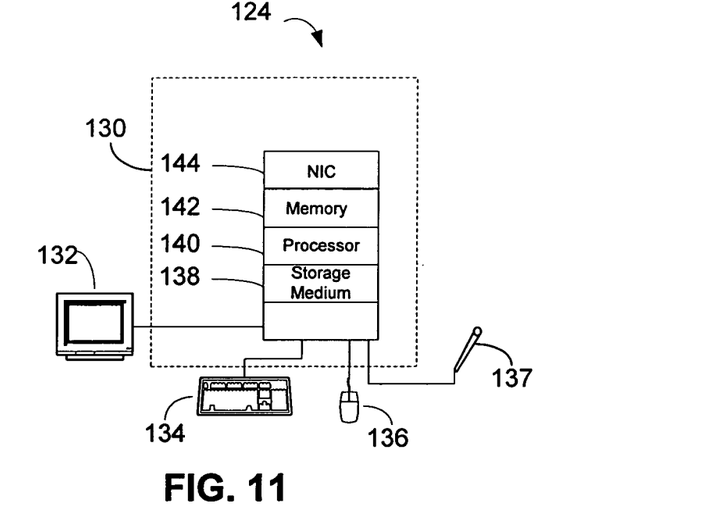
FIG. 11 is a block diagram of a computer system that can be used to implement the method of the present invention.

Moving to FIG. 11, the computer system 124 for executing a computer program in accordance with the present invention is illustrated. The computer system 124 includes a computer 130 for processing data, and a display 132 for viewing system information. The display may be any type of display currently available, such as a flat panel liquid crystal display (LCD) or a cathode ray tube (CRT) display, or any display subsequently developed. A keyboard 134 and pointing device 136 may be used for data entry, data display, screen navigation, etc. The keyboard 134 and pointing device 136 may be separate from the computer 130 or they may be integral to it. A computer mouse or other device that points to or otherwise identifies a location, action, etc., e.g., by a point and click method or some other method, are examples of a pointing device.

Alternatively, a touch screen (not shown) may be used in place of the keyboard 134 and pointing device 136. A touch screen is well known by those skilled in the art and will not be described in detail herein. Briefly, a touch screen implements a thin transparent membrane over the viewing area of the display 132. Touching the viewing area sends a signal to the computer 130 indicative of the location touched on the screen. The computer 130 may equate the signal in a manner equivalent to a pointing device and act accordingly. For example, an object on the display 132 may be designated in software as having a particular function (e.g., view a different screen). Touching the object may have the same effect as directing the pointing device 136 over the object and selecting the object with the pointing device, e.g., by clicking a mouse. Touch screens may be beneficial when the available space for a keyboard 134 and/or a pointing device 136 is limited.

A voice input device, such as a microphone, may be optionally included with the computer system 124. The voice input device is coupled to a sound input section (not shown) of the computer system 124. The voice input device 137 can be used to accept voice input from a user, such as the surgeon 22. Voice recognition software, executed by the computer system 124, can convert the voice data received via the voice input device 137 into meaningful data. For example, the voice data can be interpreted by the computer system 124 as one or more commands, wherein the computer system 124 executes specific functions based on the commands. Additionally, the voice input device 137 can be used to enter data into the data acquisition module 16. This can be done in conjunction with the keyboard and pointing device, or as an alternative thereto.

Included in the computer 130 is a storage medium 138 for storing information, such as application data, screen information, programs, etc. The storage medium 138 may be used in addition to the aforementioned storage medium 20 (FIG. 1), or it may be used in place of the storage medium 20. The storage medium 138 may be a hard drive, for example. A processor 140, such as an AMD Athlon 64® processor or an Intel Pentium IV® processor, combined with a memory 142 and the storage medium 138 execute programs to perform various functions, such as data entry, numerical calculations, screen display, system setup, etc. A network interface card (NIC) 144 allows the computer 130 to communicate with devices external to the system 124.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity. As will be appreciated, the various computer codes for carrying our the processes herein described can be embodied in computer-readable media.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A computer implemented system for graphically depicting a region for a treatment instrument with respect to a patient, comprising:
   a processor configured to:
   generate a first type of electrophysiological data of an individual patient based on a first dataset obtained using a first data collection method, the first type of electrophysiological data being a function of at least one varied treatment characteristic of the treatment instrument and describing whether an application of the treatment instrument in a region produces a desirable first effect, an undesirable first effect, or an indifferent first effect that is neither completely desirable nor completely undesirable;
   generate a second type of electrophysiological data of the individual patient based on a second dataset obtained using a second data collection method, the second data collection method different from the first data collection method, the second type of electrophysiological data being a function of the at least one varied treatment characteristic of the treatment instrument and describing whether said application of the treatment instrument in said region produces a desirable second effect, an undesirable second effect, or an indifferent second effect that is neither completely desirable nor completely undesirable, the respective second effects being different from the respective first effects; and
   generate a graphical depiction of a combination of the first and second types of electrophysiological data of the individual patient to produce a mixed display of both the first and second types of electrophysiological data, wherein the graphical depiction comprises a continuous graphical representation indicating whether said application of the treatment instrument in said region produces a desirable overall effect, an undesirable overall effect, or an indifferent overall effect that is neither completely desirable nor completely undesirable, the respective overall effects incorporating the respective first and the respective second effects, and wherein the respective overall effects are represented in the graphical depiction as a function of the at least one varied treatment characteristic and a position in the region; and
   a display for displaying the graphical depiction.

2. The system of claim 1, wherein the first and second types of electrophysiological data are normalized.

3. The system of claim 2, wherein the normalized electrophysiological data comprises interpolated data and/or extrapolated data such that data within each of the first and second types of electrophysiological data corresponds to one another.

4. The system of claim 1, wherein the combination of the first and second types of electrophysiological data is color coded based on at least two colors, wherein a first color represents a desirable effect and a second color represents an undesirable effect.

5. The system of claim 4, wherein the color codes comprise at least one additional color that represents an indifferent effect.

6. The system of claim 1, wherein the processor further directs the acquisition of the first and second types of electrophysiological data of the patient.

7. The system of claim 6, wherein the acquisition of the first and second types of electrophysiological data comprises data points that identify each of the first and second types of electrophysiological data as desirable, undesirable or indifferent, wherein the identification is based on a clinical treatment success obtainable by placing the treatment instrument in a region corresponding to the data points.

8. The system of claim 6, wherein the acquisition of the first and second types of electrophysiological data comprises data points that identify desirable, undesirable or indifferent data points, wherein the desirable and undesirable data points are identified as data points in which the first and the second types of electrophysiological data are in substantial agreement, and indifferent data points are identified as data points in which at least one of the first and second types of electrophysiological data is in disagreement with a corresponding data point of another of the first and second types of electrophysiological data.

9. The system of claim 8, further comprising color codes that identify the desirable, undesirable and indifferent data points.

10. The system of claim 9, wherein the color code comprises at least three colors to identify the respective data points.

11. The system of claim 6, wherein the acquisition of the first and second types of electrophysiological data comprises at least one of numeric data, binary data, textual data, graphical data, acoustical data, or any combination thereof.

12. The system of claim 6, wherein the processor further directs an application of a stimulation signal to a position within the patient and records measured and observed responses to the stimulation signal.

13. The system of claim 12, wherein the processor further commands a strength of the stimulation signal to be altered.

14. The system of claim 1, wherein the combination of the first and second types of electrophysiological data is color coded based on at least two colors, wherein colors of the color code represent qualitative and quantitative meanings with respect to a clinical treatment success of the placing the treatment instrument in the desired region.

15. The system of claim 1, wherein the processor applies a weighting coefficient to each of the first and second types of electrophysiological data, wherein each weighting coefficient affects the respective electrophysiological data's contribution to the graphical depiction.

16. The system of claim 1, wherein the processor applies thresholding to at least one of the first and second types of electrophysiological data, wherein thresholding includes designating a region to be completely desirable or completely undesirable based on a tendency of the region to be more desirable or more undesirable.

17. The system of claim 1, wherein the processor applies leveling to the graphical depiction, wherein leveling comprises introducing a non-linearity to at least one of the first and second types of electrophysiological data.

18. The system of claim 1, wherein the processor overlays the graphical depiction with anatomical image data of the patient.

19. The system of claim 18, wherein a two-dimensional or a three-dimensional pattern is overlaid with the anatomical image data.

20. The system of claim 1, wherein the processor generates a two-dimensional patterned graph of the graphical depiction.

21. The system of claim 1, further comprising a positioning means for positioning at least one electrode, said positioning means being communicatively coupled to and under the control of the processor.

22. The system of claim 21, wherein the positioning means is a stereotactic arc system or a frameless holding arm.

23. A non-transitory computer-readable program storage medium storing a computer program which, when executed on a processor of a computer or loaded into the memory of a computer, causes the computer to perform a computer implemented method for graphically depicting a desired region for a treatment instrument with respect to a patient, comprising:
generating a first type of electrophysiological data of an individual patient based on a first dataset obtained using a first data collection method, the first type of electrophysiological data being a function of at least one varied treatment characteristic of the treatment instrument and describing whether an application of the treatment instrument in a region produces a desirable first effect, an undesirable first effect, or an indifferent first effect that is neither completely desirable not completely undesirable;
generating a second type of electrophysiological data of the individual patient based on a second dataset obtained using a second data collection method, the second data collection method different from the first data collection method, the second type of electrophysiological data being a function of the at least one varied treatment characteristic of the treatment instrument and describing whether said application of the treatment instrument in said region produces a desirable second effect, an undesirable second effect, or an indifferent second effect that is neither completely desirable nor completely undesirable, the respective second effects being different from the respective first effects;
generating, a graphical depiction of a combination of the first and second types of electrophysiological data of the individual patient to produce a mixed display of both the first and second types of electrophysiological data, wherein the graphical depiction comprises a continuous graphical representation indicating whether said application of the treatment instrument in said region produces a desirable overall effect, an undesirable overall effect, or an indifferent overall effect that is neither completely desirable not completely undesirable, the respective overall effects incorporating the respective first and the respective second effects, and wherein the respective overall effects are represented in the graphical depiction as a function of the at least one varied treatment characteristic and a position in the region; and
controlling a display to display the graphical depiction.

24. The non-transitory computer-readable program storage medium of claim 23, wherein the computer implemented method further comprises normalizing the first and second types of electrophysiological data.

25. The non-transitory computer-readable program storage medium of claim 24, wherein the normalizing includes interpolating and/or extrapolating data such that data within each of the first and second types of electrophysiological data corresponds to one another.

26. The non-transitory computer-readable program storage medium of claim 23, wherein the computer implemented method further comprises color coding each of the first and second types of electrophysiological data based on at least two colors, wherein a first color represents a desirable effect and a second color represents an undesirable effect.

27. The non-transitory computer-readable program storage medium of claim 23, wherein the computer implemented method further comprises applying a weighting coefficient to each of the first and second types of electrophysiological data, wherein each weighting coefficient affects the respective electrophysiological data's contribution to the graphical depiction.

28. The non-transitory computer-readable program storage medium of claim 23, wherein the computer implemented method further comprises overlaying the graphical depiction with anatomical image data of the patient.

29. A system for graphically depicting a desired region for a treatment instrument with respect to a patient, comprising:
a data acquisition module, wherein the data acquisition module is configured to generate as an input a first type of electrophysiological data of an individual patient based on a first dataset obtained using a first data collection method, the first type of electrophysiological data being a function of at least one varied treatment characteristic of the treatment instrument and describing whether an application of the treatment instrument in a region produces a desirable first effect, an undesirable first effect, or an indifferent first effect that is neither completely desirable nor completely undesirable and generate a second type of electrophysiological data of the individual patient based on a second dataset obtained using a second data collection method, the second data collection method different from the first data collection method, the second type of electrophysiological data being a function of the at least one varied treatment characteristic of the treatment instrument and describing whether said application of the treatment instrument in said region produces a desirable second effect, an undesirable second effect, or an indifferent second effect that is neither completely desirable nor completely undesirable, the respective second effects being different from the respective first effects;
a storage medium for storing the different types of electrophysiological data;
a data visualization module, wherein the data visualization module retrieves each of the different types of electrophysiological data from the storage medium and generates a graphical depiction of a combination of the first and second types of electrophysiological data of the individual patient to produce a mixed display of both the first and second types of electrophysiological data, wherein the graphical depiction comprises a continuous graphical representation indicating whether said application of the treatment instrument in said region produces a desirable overall effect, an undesirable overall effect, or an indifferent overall effect that is neither completely desirable nor completely undesirable, the respective overall effects incorporating the respective first and the respective second effects, and wherein the respective overall effects are represented in the graphical depiction as a function of the at least one varied treatment characteristic and a position in the region; and a display for displaying the graphical depiction.

30. The system of claim 29, wherein the data visualization module comprises a summarization control circuit, the summarization control circuit applying a weighting coefficient to each of the first and second types of electrophysiological data.

* * * * *